United States Patent
Pedrazzini

(10) Patent No.: US 8,132,837 B2
(45) Date of Patent: Mar. 13, 2012

(54) CONTAINER TRANSFER APPARATUS WITH AUTOMATIC POSITIONING COMPENSATION

(75) Inventor: Gianandrea Pedrazzini, Paradiso (CH)

(73) Assignee: Inpeco IP Ltd., Valletta (MT)

( * ) Notice: Subject to any disclaimer, the term of this patent is extended or adjusted under 35 U.S.C. 154(b) by 256 days.

(21) Appl. No.: 12/517,474

(22) PCT Filed: Dec. 4, 2006

(86) PCT No.: PCT/EP2006/069287
§ 371 (c)(1),
(2), (4) Date: Jul. 27, 2009

(87) PCT Pub. No.: WO2008/067847
PCT Pub. Date: Jun. 12, 2008

(65) Prior Publication Data
US 2010/0045058 A1  Feb. 25, 2010

(51) Int. Cl.
*B66C 1/42* (2006.01)
(52) U.S. Cl. ............ 294/86.4; 269/71; 269/254 CS; 29/81.1
(58) Field of Classification Search ............ 294/86.4, 294/119.1; 414/785, 621, 610, 617, 618; 269/43, 71, 254 CS; 29/81.1
See application file for complete search history.

(56) References Cited

U.S. PATENT DOCUMENTS

| | | | |
|---|---|---|---|
| 2,815,623 A * | 12/1957 | Holstebroe et al. | 53/58 |
| 6,060,022 A | 5/2000 | Pang et al. | |
| 6,217,093 B1 * | 4/2001 | Neutel et al. | 294/87.1 |
| 6,264,419 B1 | 7/2001 | Schinzel | |
| 6,458,324 B1 * | 10/2002 | Schinzel | 422/65 |
| 6,485,285 B1 * | 11/2002 | Shiotani | 425/139 |
| 6,652,015 B1 * | 11/2003 | Carney et al. | 294/86.4 |
| 7,131,361 B2 * | 11/2006 | Nakajima | 83/100 |
| 7,302,755 B2 * | 12/2007 | Ricketson | 29/743 |
| 2002/0102736 A1 | 8/2002 | Kittock et al. | |

FOREIGN PATENT DOCUMENTS

EP   0 973 039 A3   1/2000

* cited by examiner

*Primary Examiner* — Saul Rodriguez
*Assistant Examiner* — Stephen Vu
(74) *Attorney, Agent, or Firm* — Birch, Stewart, Kolasch & Birch, LLP

(57) ABSTRACT

An apparatus for transferring a specimen container from a departure support to a container which includes a gripper supporting frame and a container gripper selectively movable with respect to the frame between an upper position and lower position in which gripper fingers of the container gripper are able to catch a container in a departure support or to leave the container in a container carrier. The apparatus further includes a gripper blocking element movable between a work position, in which said gripper blocking element stops the movement of the container gripper towards the lower position in an intermediate position between the upper and lower positions, and a rest position in which the gripper blocking element allows the container gripper to reach the lower position sliding along the lateral surface of the container.

9 Claims, 5 Drawing Sheets

# CONTAINER TRANSFER APPARATUS WITH AUTOMATIC POSITIONING COMPENSATION

BACKGROUND OF THE INVENTION

The present invention concerns a container transfer apparatus which allows automatic compensation of possible erroneous positioning of the container in a container carrier.

As used herein, the term "container" means an article that contains a biological specimen and has a tubular opening for access of the contents, e.g. a test tube.

At the entry in an automated clinical chemistry laboratory it is requested to transfer a specimen container from a departure support, such as an input/output module (IOM), to a container carrier (for example as disclosed in PCT application No. PCT/EP2006/067294 of the same Applicant) which is then moved by a motorized conveyor belt through a succession of workcells.

There are known container transfer apparatus comprising a fixed frame and a container gripper movable between an upper position and a lower position.

When in the lower position the container gripper grips a container placed in the departure support by means of movable fingers, then upraises and is moved over a container carrier placed on a conveyor belt.

Finally the container gripper goes down to position the gripped container inside the container carrier.

The vertical distance of the container gripper between the upper position and the lower position is standard, while the vertical position of the container in the departure support, namely the IOM, may vary as for human mistakes that do not grant the correct contact of the bottom of the container with the abutment plane surface of the departure support.

If the container is not correctly positioned in the departure support, the gripper fingers of the container gripper catch the container lower than usual.

As a result, when the container gripper places the container into the container carrier, the bottom of the container is not in contact with the abutment plane surface of the carrier, that is the container is not correctly positioned in the carrier.

An incorrect positioning of the container in its carrier may cause a lot of problems during its passage through the several workcells.

SUMMARY OF THE INVENTION

Object of the present invention is to provide a container transfer apparatus which allows sure correct positioning of the container in the container carrier.

According to the invention said object is achieved by an apparatus for transferring a specimen container from a departure support to a container carrier, comprising a gripper supporting frame and a container gripper selectively movable with respect to said frame between an upper position and a lower position in which gripper fingers of the container gripper are able to catch a container in a departure support or to leave the container in a container carrier, characterized by comprising gripper blocking means movable between a work position, in which said blocking means stop the movement of the container gripper towards the lower position in an intermediate position between said upper and lower positions, and a rest position in which said gripper blocking means allow the container gripper to reach the lower position sliding along the lateral surface of the container.

With the blocking means in the work position the container gripper is therefore stop in an intermediate position in which the gripper fingers can catch the container in the departure support whichever is its vertical position. The container gripper is then moved above a destination carrier and with the blocking means in the rest position it is lowered to the lower position where it leaves the container with the container bottom in contact with the abutment plane surface of the carrier by making the gripper fingers to slide vertically along the lateral surface of the container. In this way, possible container positioning mistakes are prevented.

BRIEF DESCRIPTION OF THE DRAWINGS

The characteristics and advantages of the present invention will appear evident from the following detailed description of an embodiment thereof illustrated as non-limiting example in the enclosed drawings, in which.

DETAILED DESCRIPTION OF THE INVENTION

Figure 1:
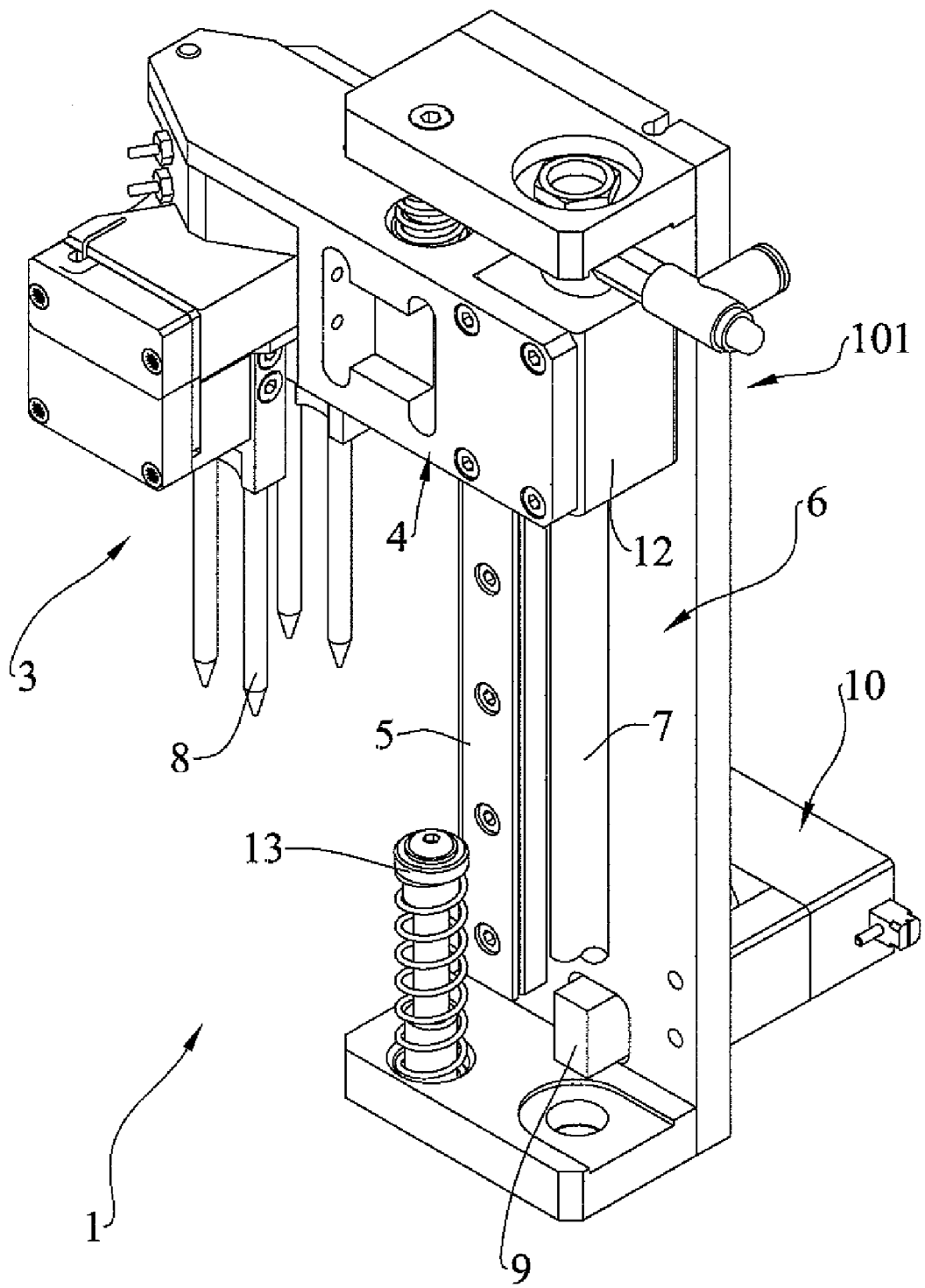
FIG. 1 is a perspective view of an apparatus according to the present invention with the blocking means in the work position.

A container transfer apparatus 1 is shown in FIGS. 1-5 for the transfer of a container 2 from a departure support of an input/output module to a container carrier 20 (destination support, FIG. 6) movable on a motorized conveyor belt.

The transfer apparatus comprises a container gripper 3 selectively movable by a carriage 4 along a vertical guide 5 and a vertical guiding bar 7 of a supporting frame 6 between an upper position 101 and a lower position 103. The container gripper 3 includes movable catching fingers 8.

The apparatus 1 also comprises a blocking cursor 9, which is driven to be selectively movable between a rest position (FIG. 2) and a work position (FIG. 1), and shock absorber members 13. The cursor 9 is driven by a pneumatic device 10 comprising a pneumatic piston 11.

In said work position the cursor 9 engages a rigid member 12 fixed to the carriage 4, so that the container gripper 3 is stop in an intermediate position 102 between said upper position 101 and said lower position 103.

Figure 3:
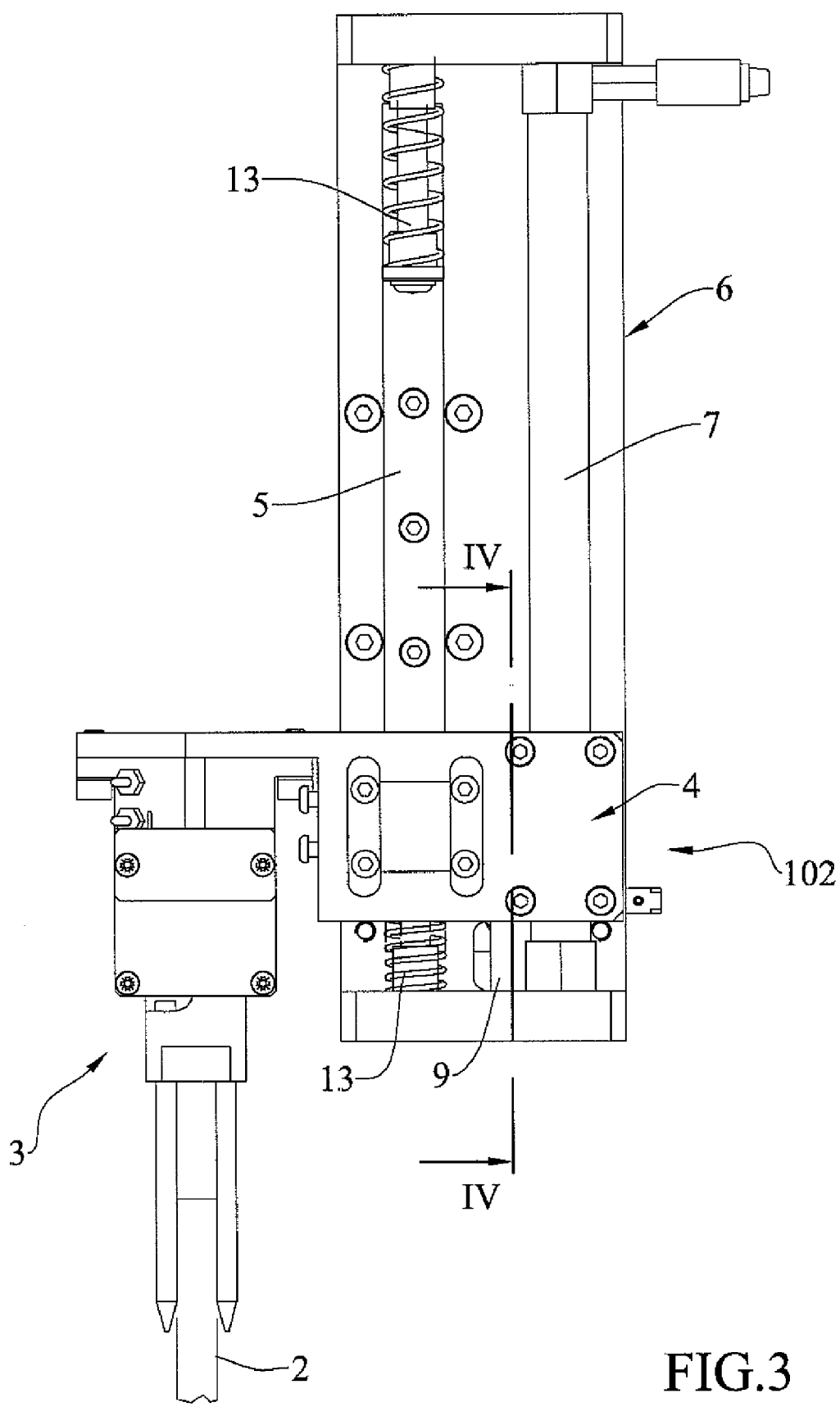
FIG. 3 is a lateral view of the apparatus with the container gripper in the intermediate position.
Figure 4:
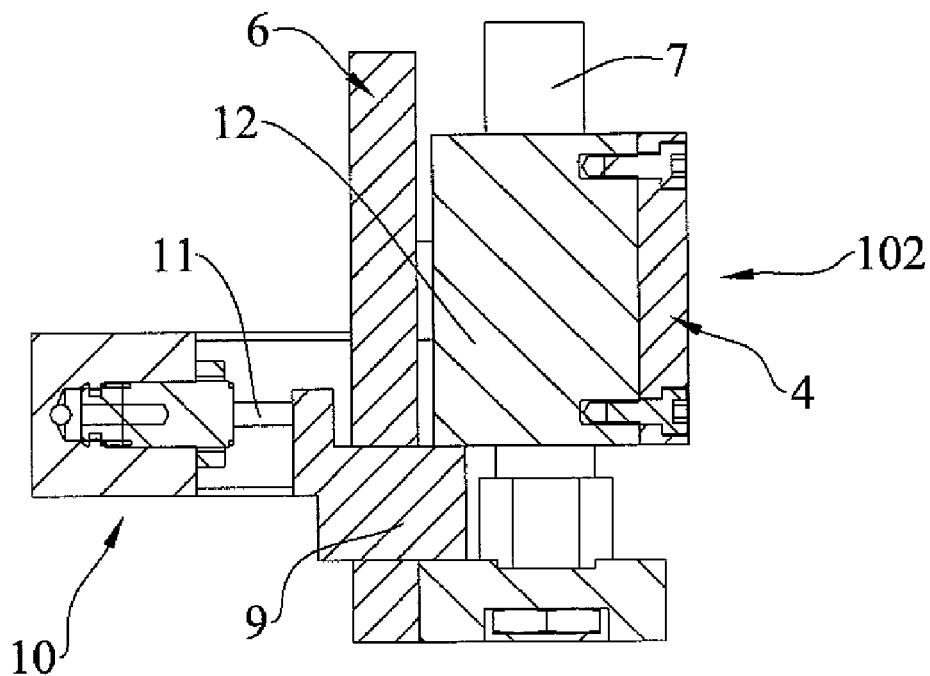
FIG. 4 is a sectional view according to line IV-IV of FIG. 3.

Firstly considering the container gripper 3 in the upper position 101 over a specimen container 2 positioned in a departure support, the container gripper 3 goes down to the intermediate position 102 (FIGS. 3 and 4) with the cursor 9 in the work position of FIGS. 1, 3 and 4 engaged with the rigid member 12.

The vertical distance between the intermediate position 102 and the lowered position 103 (see FIGS. 4-5) is enough to achieve the aforementioned object of the invention.

Thus, the container 2 is caught higher than if the cursor 9 were in the rest position.

Figure 6:
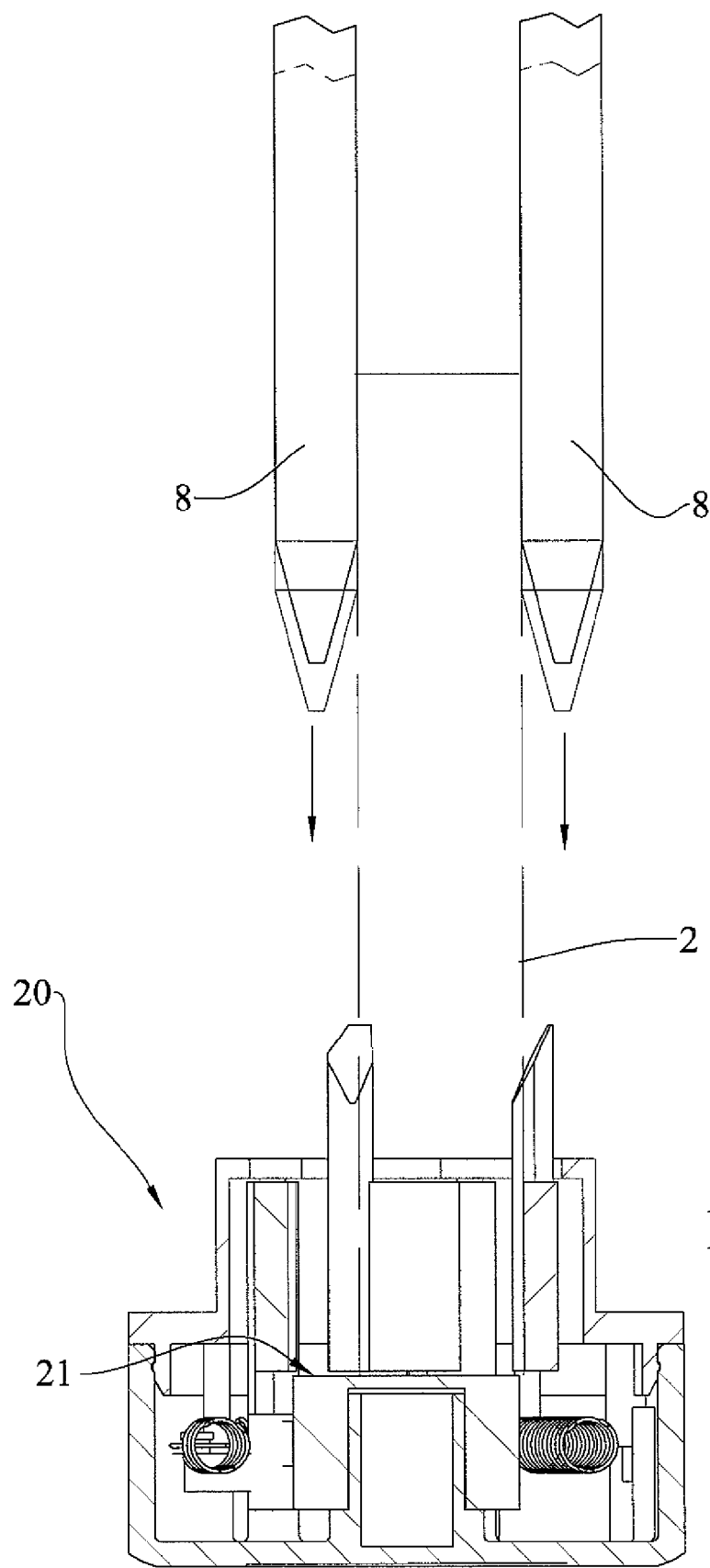
FIG. 6 is a lateral sectional view showing the positioning of the container onto the destination support.

Then the container 2 is upraised and the frame 6 is driven to put the container 2 over the container carrier 20 (FIG. 6).

Figure 2:
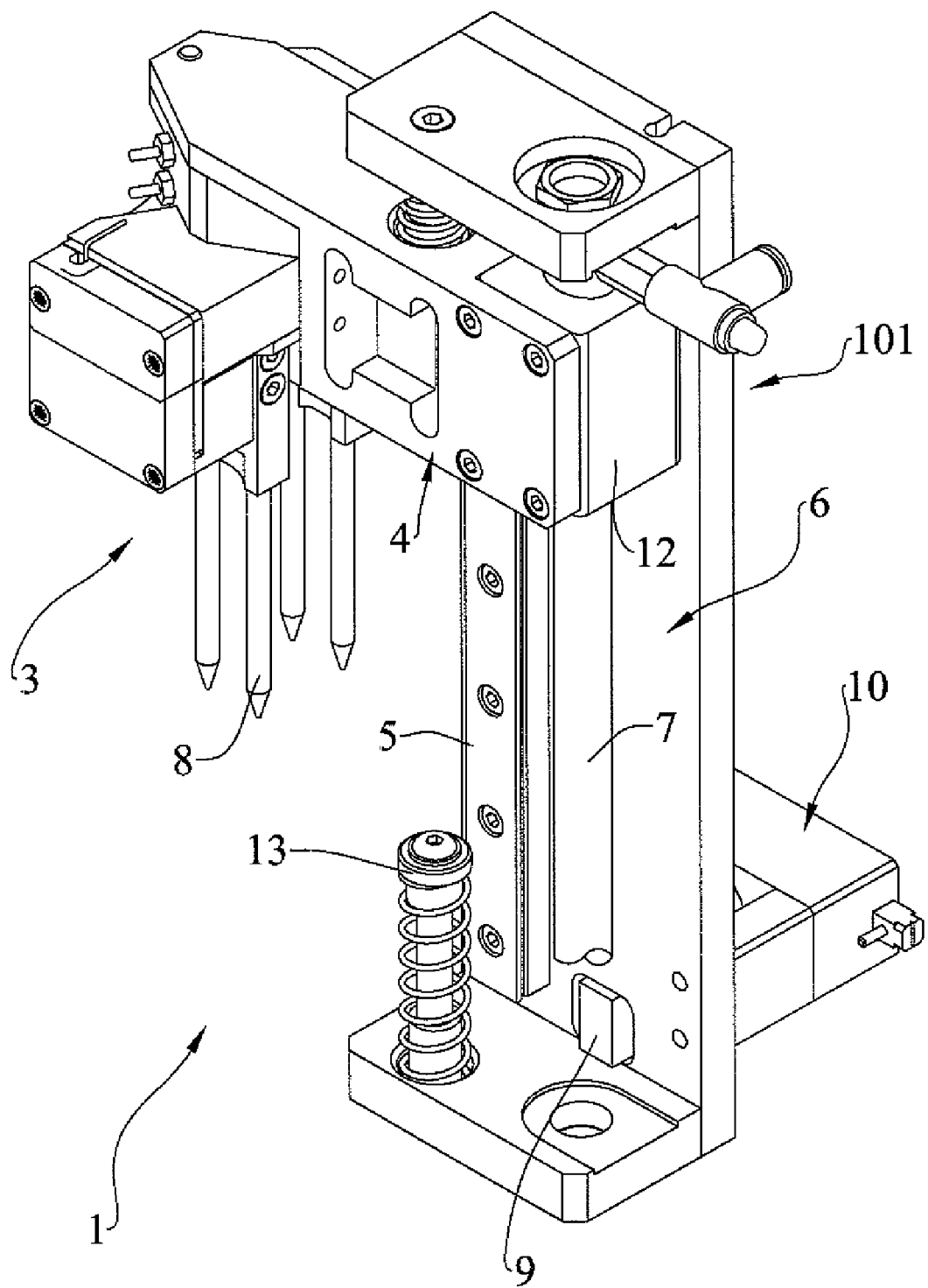
FIG. 2 is a perspective view of an apparatus according to the present invention with the blocking means in the rest position.
Figure 5:
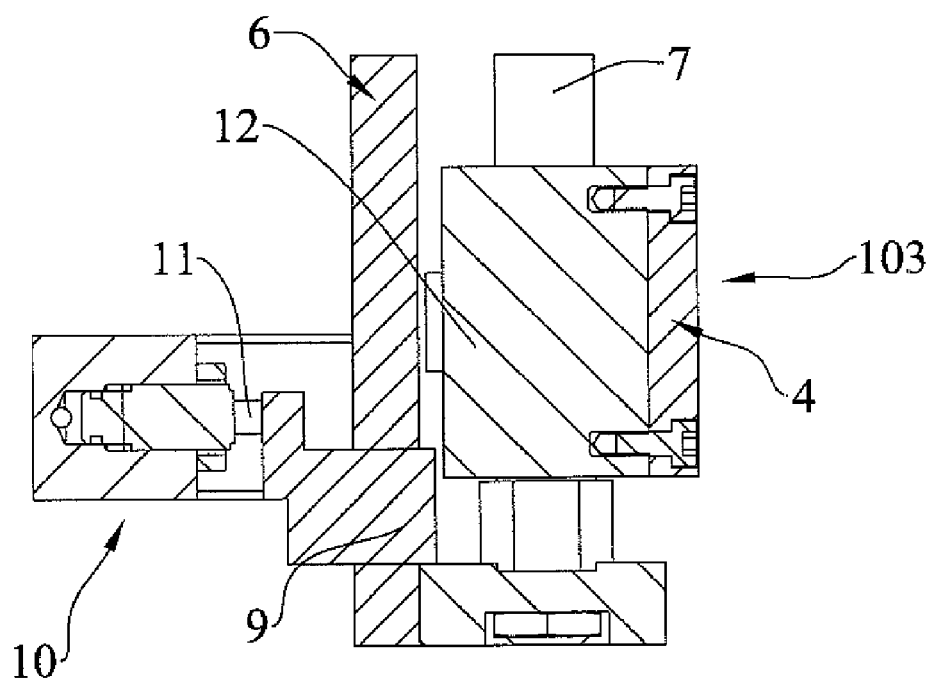
FIG. 5 is a sectional view similar to FIG. 4, but with the blocking means in a rest position, thus with the container gripper in the lowered position.

The container gripper 3 is now moved to the lower position 103, with the cursor 9 being in the rest position of FIGS. 2 and 5.

If the bottom of the container 2 touches the abutted plane surface 21 of the container carrier 20 before the end of the run of the gripper 3, the fingers 8 slide on the external lateral surface of the container 2 which is already correctly positioned (FIG. 6).

Obviously the pushing force of the gripper 3 is higher than the catching force of the fingers 8.

Finally the gripper 3 leaves the container correctly positioned.

With a very simple device, a perfect positioning into the destination support is achieved.

The invention claimed is:

1. An apparatus for transferring a specimen container from a departure support to a container carrier, comprising:
   - a gripper supporting frame and a container gripper selectively movable with respect to said gripper supporting frame between an upper position and a lower position in which gripper fingers of the container gripper are able to catch a container in a departure support or to leave the container in a container carrier; and
   - gripper blocking means movable between a work position, in which said gripper blocking means stops movement of the container gripper towards the lower position, in an intermediate position between said upper and lower positions, and a rest position in which said gripper blocking means allows the container gripper to reach the lower position sliding along a lateral surface of the specimen container if the bottom of said container touches an abutted surface of the container carrier before said container gripper reaches the lower position.

2. The apparatus according to claim 1, wherein said gripper blocking means comprise a blocking cursor which is movable in a transversal direction with respect to the direction of movement of the container gripper between the upper and lower positions.

3. The apparatus according to claim 2, wherein said container gripper is fixed to a carriage movable along a vertical guiding means of said gripper supporting frame.

4. The apparatus according to claim 2, wherein said gripper supporting frame comprises shock absorbing means for said container gripper.

5. The apparatus according to claim 1, wherein said container gripper is fixed to a carriage movable along a vertical guiding means of said gripper supporting frame.

6. The apparatus according to claim 5, wherein said carriage includes a cursor engageable part.

7. The apparatus according to claim 6, wherein said gripper supporting frame comprises shock absorbing means for said container gripper.

8. The apparatus according to claim 5, wherein said gripper supporting frame comprises shock absorbing means for said container gripper.

9. The apparatus according to claim 1, wherein said gripper supporting frame comprises shock absorbing means for said container gripper.

* * * * *